(12) United States Patent
Wong et al.

(10) Patent No.: US 6,224,868 B1
(45) Date of Patent: *May 1, 2001

(54) REAGENT AND PROCESSES FOR TARGETING MUTANT EPIDERMAL GROWTH FACTOR RECEPTORS

(75) Inventors: Albert J. Wong; David K. Moscatello, both of Philadelphia, PA (US)

(73) Assignee: Thomas Jefferson University, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/861,423

(22) Filed: May 21, 1997

Related U.S. Application Data (63) Continuation-in-part of application No. 08/347,520, filed on Nov. 28, 1994, now abandoned, and a continuation-in-part of application No. PCT/US95/15401, filed on Nov. 28, 1995.

(51) Int. Cl.[7] .................................................. A61K 39/00

(52) U.S. Cl. .................................... 424/184.1; 424/185.1; 424/277.1

(58) Field of Search ............................... 435/68.1; 514/2; 424/184.1, 185.1, 277.1

(56) References Cited

U.S. PATENT DOCUMENTS

| | | | |
|---|---|---|---|
| 5,212,290 | * 5/1993 | Vogelstein et al. | 530/387.7 |
| 5,894,018 | 4/1999 | Davila et al. | 424/198 |

FOREIGN PATENT DOCUMENTS

| | | |
|---|---|---|
| US90/04489 | 3/1991 | (WO) . |

OTHER PUBLICATIONS

Baltz. Vaccines for the treatment of cancer. Am. J. Health–Syst. Pharm. 52:2574–2585, Nov. 1995.*
Moscatello et al. A Naturally Occurring Mutant Human Epidermal Growth Factor Receptor as a Target for Peptide Vaccine Immunotherapy of Tumors. Canc. Res. 57:1419–1424, Apr. 1997.*
Muller et al. Specific antibosy response towards predicted epitopes of the epidermal growth factor receptor indiced by a thermostable synthetic peptide adjuvant conjugate. Clin. Exp. Immunol. 78(3):499–504, Dec. 1989.*
Brady et al., "Malignant Astrocytomas Treated with Iodine–125 Labeled Monoclonal Antibody 425 Against Epidermal Growth Factor Receptor: A Phase II Trial",*Intl J. Rad. Onc, Biol, Phys.* 1992, 22(1), 225–30.
Cole et al., "The EBV–Hybridoma Technique and Its Application to Human Lung Cancer", *Monoclonal Antibodies and Cancer Therapy*, Alan R. Liss, Inc., pp 77–96.
Harris, A.L. "Epidermal Growth Factor Receptor in Human Breast Cancer" *Recent Results in Cancer Research* 1989, 113, 70–77.
Hellstrom, I. and Hellstrom K.E., "Tumor Immunology: An Overview", *Annals of New York Acad Sci* 1993, 690, 24–33.
Humphrey et al., "Amplification and Expression of the Epidermal Growth Factor Receptor Gene in Human Glioma Xenografts", *Cancer Research* 1988, 48, 2231–2238.
Humphrey et al., "Anti–synthetic peptide antibody reacting a the fusion junction of deletion–mutant epidermal growth factor receptors in human glioblastoma", *Proc Natl Acad Sci USA* 1990, 87, 4207–4211.
Kohler and Milstein, "Continuous cultures of fused cells secreting antibody of predefined specificity", *Nature* 1975, 256,495–497.
Kosbor et al., "The production of monoclonal antibodies from human lymphocytes", *Immunology Today* 1983, 4, 72.
Libermann et al., "Amplification, enhanced expression and possible rearrangement of EGF receptor gene in primary human brain tumours of glial orgin", *Nature* 1985, 313(5998), 144–7.
Masui et al., "Cytotoxicity against Human Tumor Cells Mediated by the Conjugate of Anti–Epidermal Growth Factor Receptor Monoclonal Antibody to Recombinant Ricin A Chain", *Cancer Research* 1989, 49(13), 3482–8.
Mendelsohn, J., "The epidermal growth factor receptor as a target for therapy with antireceptor monoclonal antibodies", *Sem Can Biol* 1990, 1(5), 339–44. Abstract.
Mendelsohn, J., "Anti–Epidermal Growth Factor Receptor Monoclonal Antibodies as Potential Anti–Cancer Agents",*J. Steroid Biochem & Mol Biol* 1990, 37(6), 889–92.
Morrison, "Suppression of Basic Fibroblast Growth Factor Expression by Antisense Oligodeoxynucleotides Inhibits the Growth of Transformed Human Astrocytes", *J. Biol Chem* 1991, 266(2), 728–34.
Moroni et al., "EGF–R antisense RNA Blocks Expression of the Epidermal Growth Factor Receptor and Suppresses the Transforming Phenotype of a Human Carcinoma Cell Line", *J. Biol Chem* 1992, 267, 2714–2723.
Sawamura, Y and DeTribolet, N., "Immunotherapy of brain tumors", *J. Neurosurgical Sci* 1990, 34(3–4), 265–78. Abstract.
Trojan et al., "Treatment and Prevention of Rat Glioblastoma by Immunogenic C6 Cells Expressing Antisense Insulin–Like Growth Factor I RNA", *Science* 1993, 259, 94–97.

(List continued on next page.)

*Primary Examiner*—John Ulm
(74) *Attorney, Agent, or Firm*—Seidel Gonda, Lavorgna & Monaco, P.C.

(57) ABSTRACT

Vaccines comprising peptides from a fusion junction present in a mutant human EGF receptor and methods of using these vaccines in the inhibition of tumor formation and enhancement of tumor regression are provided. Cell lines which overexpress a Type III mutant EGF receptor and methods of producing these cell lines are also provided. In addition, antibodies raised against peptides expressed by these cell lines are provided. Further, antisense oligonucleotides targeted to a mutant EGF receptor which decreases expression of a mutant EGF receptor are disclosed.

12 Claims, 1 Drawing Sheet

OTHER PUBLICATIONS

Ullrich et al., "Human epidermal growth factor receptor cDNA sequence and aberrant expression of the amplified gene in A431 epidermoid carcinoma cells", *Nature* 1984 309, 418–425.

Wong et al., "Structural alterations of the epidermal growth factor receptor gene in human gliomas", *Proc Natl Acad Sci USA* 1992, 89, 2965–2969.

Wong et al., "Increased expression of the epidermal growth factor receptor gene in malignant gliomas is invariably associated with gene amplification", *Proc Natl Acad Sci USA* 1987 84(19), 6899–903.

Yamada et al., "Reduction of EGF Receptor Levels in Human Tumor Cells Transfected with an Antisense RNA Expression Vector", *Exp Cell Res* 1989, 184, 90–98.

Bigner et al., "Characterization of the Epidermal Growth Factor Receptor in Human Glioma Cell Lines and Xenografts", *Cancer Res.* 1990, 50, 8017–8022.

Chomczynski, P. and Sacchi, N., "Single–Step Method of RNA Isolation by Acid Guanidinium Thiocyanate–Phenol–Chloroform Extraction", *Anal Biochem*, 1987, 162,156–159.

Ekstrand et al., "Functional characterization of an EFG receptor with a truncated extracellular domain expressed in glioblastomas with EGFR gene amplification", *Oncogene* 1994, 9, 2313–2320.

Harris, A.L., "Epidermal Growth Factor Receptor in Human Breast Cancer", *Recent Results in Cancer Research* 1989, 113, 70–77.

Milstein, "Continuous cultures of fused cells secreting antibody of predefined specificity", *Nature* 1975, 256, 495–497.

Moscatello et al., "Frequent Expression of a Mutant Epidermal Growth Factor Receptor in Multiple Human Tumors", *Cancer Res.* 1995, 55, 5536–5539.

Wikstrand et al., "Human Fetal Brain Antigen Expression Common to Tumors of Neuroectodermal Tissue Origin", *J. Neuroimmunol.* 1982, 3, 4362.

Wikstrand et al., "Investigation of a synthetic epetide as immunogen for a varian epidermal growth facotr receptor associated with glimoas", *J. Neuroimmunilo.* 1993, 46, 165–174.

Yamazaki et al., "A Deletion Mutation within the Ligand Binding Domain is Responsible for Activation of Epidermal Growth Factor Receptor Gene in Human Brain Tumors", *Jpn. J. Cancer Res.* 1990, 81, 773–779.

Wong et al., "Increased expression of the epidermal growth factor receptor gene in malignant gliomas in invariably associated with gene amplification", *Pro Natl Sci USA* 1987 84(19), 6899–903.

Yamada et al., "Reduction of EGF Receptor Levels in Human Tumor Cells Transfected with an Antisense RNA Expression Vector", *Exp Cell Res* 1989, 184, 90–98.

Bigner et al, "Characterization of the Epidermal Growth Factor Receptor in Human Glioma Cell Lines and Xenografts", *Cancer Res.* 1990, 50, 8017–8022.

Chomczynski, P. and Sacchi, N., "Single–Step Method of RNA Isolation by Acid Guanidinium Thiocyanate–Phenol–Chloroform Extraction", *Anal Biochem.* 1987, 162,156–159.

Ekstrand et al., "Functional Characterization of an EPG receptor with a truncated extracellular domain expressed in glioblastomas with EGFR gene amplification", *Oncogene* 1994, 9, 2313–2320.

Harris, A.L., "Epidermal Growth Factor Receptor in Human Breast Cancer", *Recent Results in Cancer Research* 1989, 113, 70–77.

Millstein, "Continuous cultures of fused cells secreting antibody of predefined specificity", *Nature* 1975, 256, 495–497.

Moscatello et al., "Frequent Expression of a Mutant Epidermal Growth Factor Receptor in Multiple Human Tumors", *Cancer Res.* 1995, 55, 5536–5539.

Wikstrand et al., "Human Fetal Brain Antigen Expression Common to Tumors of Neuroectodermal Tissue Origin", *J. Neuroimmunol.* 1982, 3, 4362.

Wikstrand et al., "Investigation of a synthetic peptide as immunogen for a variant epidermal growth factor receptor associated with glimoas", *J. Neuroimmunol.* 1993, 46, 165–174.

Yamazaki et al., "A Deletion Mutation within the Ligand Binding Domain is Responsible for Activation of Epidermal Growth Factor Receptor Gene in Human Brain Tumors", *Jpn. J. Cancer Res.* 1990, 81, 773–779.

* cited by examiner

FIG. 1

REAGENT AND PROCESSES FOR TARGETING MUTANT EPIDERMAL GROWTH FACTOR RECEPTORS

INTRODUCTION

This application is a continuation-in-part of Ser. No. No. 08/347,520 filed Nov. 28, 1994, now abandoned, and its PCT counterpart, Ser. No. PCT/US95/15401, filed Nov. 28, 1995.

This invention was made in the course of research sponsored by the National Institutes of Health. The U.S. Government may have certain rights in this invention.

BACKGROUND OF THE INVENTION

The success of any cancer therapy is based upon its ability to distinguish neoplastic cells from normal cells. Most current chemotherapy or radiotherapy regimens are based upon differential growth rates of tumor cells. In practice, such therapies have been very successful in treating some cancers, but for many other cancers current treatments are either palliative in nature or in the long term are ineffectual. Progress in brain tumor therapy has been especially poor as the survival curve has not appreciably changed in over 60 years. Some progress has been made using biologically based modalities such as harvesting a patient's immune system or therapeutics based upon recent research in molecular biology. However, the specificity of these therapeutics for cancerous cells is poor. Much of the research in biology based therapies has focused on defining tumor specific alterations.

The idea of utilizing a patient's own immune system to destroy a tumor is perhaps the oldest biologically based cancer therapy in use. The success of this approach rests upon the identification of a suitable antigen that will elicit both a humoral and cell mediated response. Ideally, immunization should employ a tumor specific antigen which is strictly expressed on tumor cells because the immune system most efficiently recognizes an antigen that has never been encountered before (Hellstrom, I. and Hellstrom K. E., *Annals of New York Acad Sci* 1993, 690, 24–33). The identification of such antigens has been difficult; however, progress has been made recently in isolating mutated or rearranged genes. Nearly all of the alterations characterized to date, such as p53, Rb, and ras genes, affect intracellular proteins. Recent data indicate that intracellular molecule may still be recognized by cytolytic T lymphocytes; however, the relative efficiency of tumor killing is unknown.

Studies with glioma xenografts, however, have shown that protein expressed from amplified epidermal growth factor (EGF) receptor gene is on the cell surface (Humphrey et al., *Cancer Research* 1988, 48, 2231–2238). The EGF receptor gene has been shown to be amplified in 40% of glioblastoma multiform tumors (Libermann et al., *Nature* 1985, 313(5998), 144–7; Wong et al., *Proc Natl Acad Sci USA* 1987 84(19), 6899–903). This receptor has been implicated in a wide variety of tumors including those of the breast, skin and bladder (Harris, A. L. *Recent Results in Cancer Research* 1989, 113, 70–77). In the majority of these studies, increased levels of receptor message, protein or EGF binding were observed. It has also been shown that in tumors with amplification of the EGF receptor gene, the gene has frequently undergone deletion and/or rearrangement (Libermann et al., *Nature* 1985, 313(5998), 144–7; Wong et al. *Proc Natl Acad Sci USA* 1987 84(19), 6899–903).

The cDNA sequence corresponding to normal EGF receptor has been reported by Ullrich et al., in *Nature* 1984 309, 418–425. Wong et al., *Proc Natl Acad Sci USA* 1992, 89, 2965–2969 and Vogelstein and Bigner (PCT/US90/04489) characterized the genetic alterations associated with rearrangements or deletions of this gene in five malignant gliomas. They found mutant EGF receptor protein to be present in cells exhibiting three types of genetic deletion and/or rearrangement which result in a structurally altered receptor. The first class of deletions identified results in a gap in the extracytoplasmic domain near the transmembrane domain. The second class of deletions results in elimination of the distal portion of the extracytoplasmic domain of EGF receptor. The third class is characterized by a deletion of the majority of the external domain of the EGF receptor leaving substantially only the transmembrane portion and the intracytoplasmic domain. DNA sequences encoding proteins corresponding to each of these mutant classes were disclosed. Vogelstein and Bigner suggest that these DNA sequences may be introduced into a host cell by transformation or transfection and expressed using a wide variety of host/vector combinations. A number of useful expression vectors are disclosed including the lac system, the trp system, the tac system, the trc system major operator and promoter regions of phage lambda, the control region of fd coat protein, the glycolytic promoters of yeast, the promoters of yeast acid phosphatase, the promoters of the yeast a-mating factors, and promoters derived from polyoma, adenovirus, retrovirus, or simian virus, and other sequences known to control the expression of genes of prokaryotic or eukaryotic cells and their viruses of combinations thereof. Also disclosed are examples of expression hosts useful in the invention which include eukaryotic and prokaryotic hosts, such as strains of *E. coli* including *E. coli* SG-936, *E. coli* HB 101, *E. coli* W3110, *E. coli* X1776, *E. coli* X2282, *E. coli* DHI, and *E. coli* MRC1, Pseudomonas, Bacillus including *Bacillus subtilis*, Streptomyces, yeasts and other fungi, animal cells such as COS cells and CHO cells and human cells and plant cells in tissue culture. Vogelstein and Bigner suggest that the peptide product of the prokaryotic or eukaryotic hosts transformed with the DNA sequences can be employed in the production of antibodies.

The in frame deletion from nucleotide 275–1075 in the EGF receptor (referred to as class I or Type I by Vogelstein and Bigner but hereinafter referred to as Type III) was demonstrated to generate a local amino acid sequence at the fusion junction of what were distant polypeptide sequences in the intact EGF receptor. (Humphrey et al., *Proc Natl Acad Sci USA* 1990, 87, 4207–4211). A 14 amino acid peptide spanning the junction was chemically synthesized, coupled to keyhole limpet hemocyanin, and used as an immunogen in rabbits. The elicited antibody reacted specifically with the fusion peptide in ELISA. The anti-fusion antibody was purified and shown to selectively bind the glioma deletion mutant. This antipeptide antibody was suggested as an ideal candidate for tumor imaging and immunotherapy.

SUMMARY OF THE INVENTION

An object of the present invention is to provide a vaccine which inhibits tumor formation. The vaccine comprises a peptide having sufficient similarity to a fusion junction present in a mutant human EGF receptor so that an immune response to this mutant is elicited. A method of inhibiting formation of tumors bearing a naturally occurring mutant EGF receptor by administering this vaccine is also provided.

Another object of the present invention is to provide a vaccine for inducing regression of an existing tumor which comprises a peptide having sufficient similarity to a fusion junction present in a mutant human EGF receptor so that an immune response to this mutant is elicited. Administration of this vaccine provides a method of inducing regression of an existing tumor bearing a naturally occurring mutant EGF receptor.

An object of the present invention is to provide a cell line capable of overexpressing Type III mutant EGF receptors. Methods of producing these cell lines are also provided.

Another object of the present invention is to provide antibodies raised against a cell line overexpressing Type III mutant EGF receptor or a peptide or protein expressed by these cell lines.

Another object of the present invention is to provide antisense oligonucleotides targeted to a mutant EGF receptor which decrease expression of a mutant EGF receptor.

BRIEF DESCRIPTION OF THE FIGURE

The FIGURE provides DNA and peptide sequences of normal and Type III mutant EGF receptors. The upper sequence depicts the nucleotide sequence and corresponding amino acid translation according to Ullrich et al. *Nature* 1984, 309, 418–425 (SEQ ID NO: 4 and SEQ ID NO: 5 and SEQ ID NO: 9 and SEQ ID NO: 10, respectively). The lower sequence shows the resulting deletion in the Type III EGF receptor and the corresponding amino acid sequence (SEQ ID NO: 6 and SEQ ID NO: 11, respectively).

DETAILED DESCRIPTION OF THE INVENTION

Figure 1:
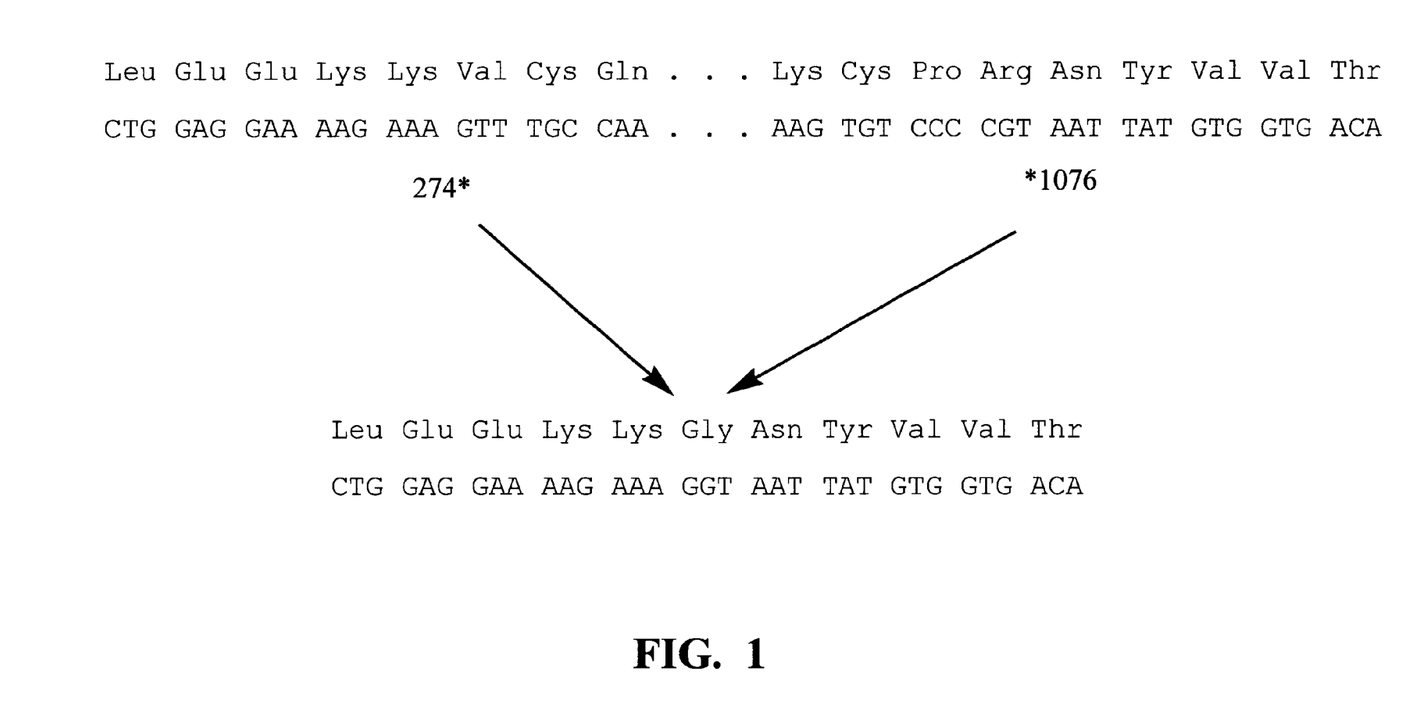

The Type III mutant EGF receptor is a deletion between nucleotides 275–1075 in the EGF receptor cDNA. This deletion results in the fusion of what were ordinarily distant sequences to generate a mutated cDNA sequence that results in the production of a novel peptide sequence at this fusion junction (FIG. 1). It is the most frequent, naturally occurring mutant EGF receptor in human tumors, where it has been reported to be present in 56% of glioblastoma tumors and 16% of non-small cell carcinomas of the lung. This receptor has also been found to be present in 78% of breast cancers (Moscatello et al. *Cancer Res.* 1995, 55, 5536–5539). Using antibodies specific to the mutant receptor, it has now been confirmed that this receptor is tumor specific for subsets of breast carcinoma, non-small cell lung carcinoma and gliomas. The receptor was not expressed in any normal tissues that were examined including elements of the peripheral, central nervous system and lymphoid system. This receptor has also been found in ovarian tumors.

In the present invention, a vaccine comprising a peptide sequence from the fusion junction present in the mutant human EGF receptor is provided. The peptide in the vaccine of the present invention must be of sufficient similarity to portions of the sequences from the two formerly distant portions of the normal EGF receptor to invoke an immune response against the Type III mutant EGF receptor. In a preferred embodiment, this peptide comprises at least an amino acid sequence proximal to and including the amino acid at position 5 of the normal EGF receptor amino acid sequence, which is a lysine, followed by a glycine and an amino acid sequence distal to and including the amino acid at position 274 of the normal EGF receptor, which is asparagine (Ullrich et al., *Nature* 1984, 309, 418–425). In a more preferred embodiment, this vaccine comprises the peptide sequence LEEKKGNYVVTDHC (SEQ ID NO: 1). As will be recognized by those of skill in the art upon this disclosure, similar peptides containing modifications in length or sequence that are capable of eliciting an immune response can also be used in the present invention. It is preferred that the peptide in the vaccine be conjugated to a carrier such as keyhole limpet hemocyanin (KLH), bovine serum albumin or human serum albumin. The vaccine of the present invention may also comprise an adjuvant. Adjuvants useful in vaccine are well known to those of skill in the art, thus, selection of an appropriate adjuvant can be performed routinely by one of skill in the art upon this disclosure. Examples of useful adjuvant include, but are not limited to, complete and incomplete Freund's, mineral gels such as aluminum hydroxide, surface active substances such as lysolecithin, pluronic polyols, polyanions, peptides and oil emulsions.

Previous workers have found that many vaccines based on peptide sequences were very poor at preventing the formation of tumors and all such peptide vaccines could not cause the regression of existing tumors. In contrast, immunization with the peptide vaccine of the present invention has now been found to protect against the formation of tumors. Mice were immunized with either the peptide vaccine or a control vaccine in Freund's complete adjuvant which was followed by immunization two weeks later in incomplete adjuvant. After another two weeks, the animals were injected with $10^7$ NM#3 HC2 20d2/c cells. Four out of sixteen mice that received the peptide vaccine developed tumors and in two of these mice the tumor progressed to a size which necessitated sacrifice. In contrast, 13 of the 15 mice that received control vaccine developed tumors, and in 9 mice, the tumor progressed to a size that necessitated sacrifice. Thus, prior vaccination with the peptide vaccine of the present invention resulted in a significant decrease in the overall incidence of tumor formation and also affected the ultimate tumor size. Several of the animals that had received the peptide vaccine were rechallenged with $10^7$ HC2 20d2/c cells at periods six months to one year later. No tumor formation was noted.

It was also found that the peptide vaccine enhances the rejection of established tumors. Sixty mice were injected with $10^7$ NM#3 HC2 20d2/c cells subcutaneously (s.c.). Four days later half the mice were injected with the peptide vaccine of the present invention in Freund's complete adjuvant. The other half received only a carrier and Freund's complete adjuvant. Whereas the tumors grew progressively in both sets for approximately two weeks, the mice vaccinated with the peptide vaccine exhibited enhanced tumor rejection compared with the controls from the point of vaccination onward. Vaccination also affected the ultimate tumor size as animals receiving the peptide vaccine had smaller tumor volumes. Thirteen animals required sacrifice in the control vaccinated group whereas 8 animals were sacrificed in the peptide vaccinated group. However, five of the animals from the group receiving the peptide vaccine had shown complete regression of the original tumor but approximately 40 to 50 days later developed a second tumor. These recurrent tumors were examined for expression of the EGFR type III mutant by Western blot analysis. Only one of the secondary tumors showed any evidence of EGFR type III mutant expression. In comparison, five tumors from control vaccinated mice that were sacrificed were also tested for expression of the EGFR type III mutant; only one of these tumors failed to express this protein. These results indicate that the immune system in mice receiving the peptide vaccine had been successful in eradicating any cells expressing the mutant receptor and that the subsequent tumor arose from variant cells within the original tumor mass.

CTL assays showed that lymphocytes isolated from animals immunized with the peptide vaccine of the present invention exhibited specific lysis of HC2 cells but not CO12 cells or NIH 3T3 cells, demonstrating that there was CTL activity that was specifically directed against the mutant receptor. Lymphocytes from control vaccinated mice did not show specific lysis of any of these target cells.

In addition, the present ivnention provides a series of cell lines which overexpress the Type III mutant EGF receptor. Typically, transfection of a cell line with a mammalian expression vector results in very high levels of protein expression that are stable. In the past, an unusual problem encountered by researchers attempting to express the Type III mutant receptor is that the levels of protein expression are very low and are also unstable with continuous culture. Thus, elucidating the properties of this receptor has been difficult because glioblastoma cells do not maintain high level expression of the EGFRvIII in culture (Bigner et al. *Cancer Res.* 1990, 50, 8017–8022) and transfected cell lines typically express low amounts of this mutant (Yamazaki et al. *Jpn. J. Cancer Res.* 1990, 81, 773–779; Ekstrand et al. *Oncogene* 1994, 9, 2313–2320). A unique property of the cell lines of the present invention is that they express extremely high amounts of the mutant receptor. Other researchers have obtained levels of mutant receptor of approximately 20 fold less than that expressed with the cell lines of the present invention. The cell lines of the present invention, however, express levels of the receptor ($5\times10^4$ to $2\times10^6$ receptor/cell) comparable to that found in human glial tumors (Bigner et al. *Cancer Res.* 1990, 50, 8017–8022). In addition, the expression of the mutant receptor obtained from these other cell lines is not very stable. In contrast, the cell lines of the present invention have stable expression of the mutant receptor. The receptor expressed by cell lines of the present invention is active in the absence of additional growth factor. In addition, it has been found that these cell lines produce very aggressive tumors in mice.

Also provided in the present invention is a method of preparing cell lines which overexpress the mutant Type III EGF receptor. Other studies on this mutant have been limited by the fact that low amounts of mutant receptor were present in the derived clones. Therefore, an important aspect of this method is to produce clones that express amounts of the receptor that are comparable to that found in primary glial tumors. To produce these cell lines, a clone encompassing the mutant Type III EGF receptor is identified. A plasmid construct of the full-length EGF receptor is cloned into a mammalian expression vector such as pLTR2 which drives transcription using the Moloney murine leukemia virus long terminal repeat (LTR) promoter. Other mammalian expression vectors useful in the present invention include, but are not limited to pCMV, pLSX, pSV40 and pMMTV. Mutant EGF receptor cDNA is obtained from human glial tumor cells having a deletion from nucleotides 275 to 1075. The mutant can be isolated from approximately 50% of patients with these glial tumors. Examples of specific tumor cell lines useful in the present invention include, but are not limited to, human GBM tumor D270, D317 and D256. The cDNA of the mutant Type III EGF receptor is then cloned into a phage vector. Examples of phage vectors which can be used in the present invention include, but are not limited to, lambda-Zap II, lambda-gt10, lambda-gt11, lambda-ExLox, lambda-UniZAp or lambda-GEM. A cDNA fragment of the EGF receptor containing sequences from either nucleotides 1 through 274 or nucleotides 1076–5532 is then used to identify the mutants. Once identified, the cDNA fragment encompassing the alteration is fused to the remaining portion of normal EGF receptor cDNA to produce a clone that expresses the mutant EGF receptor but is otherwise identical to the construct expressing intact normal EGF receptor. For example, a 251 bp Sst I-Dra I fragment containing the fusion junction of the clone is ligated to a 2.9 kb DraI-XhoI fragment from the plasmid pCO12. In a preferred embodiment, NIH-3T3 cells are then co-transfected with this expression plasmid. Other cell lines which can be used include, but are not limited to, BALB/3T3, RAT1, RAT2 and ROVGE 11. It is preferred that the expression plasmid used be pLTR HC2 which contains the 275–1075 deletion mutant EGF receptor. The cells are also transfected with a selection marker. Examples of selection markers useful in the present invention include, but are not limited to, neomycin resistance, hygromycin resistance, mycophenolic acid resistance and puromycin resistance. In a preferred embodiment this selection marker is an expression plasmid which encodes a gene for neomycin resistance such as pKOneo. To ensure that high levels of protein are expressed, it is preferred that ratios of expression plasmid to selection marker of at least 20:1 are used. Plated cells are transfected using a calcium phosphate method well known to those of skill in the art. Following the transfection, the cells are trypsinized and split into an appropriate selection media. By "appropriate selection media" it is meant media capable of supporting only those cells which express the selection marker. For example, in the preferred embodiment wherein the selection marker is an expression plasmid which encodes a gene for neomycin resistance such as pKOneo, the medium must contain G418 sulfate. Resistant clones are then selected and lysate prepared for screening to verify the amount of receptor expressed. Those showing high levels of expression of the receptor are then subcloned to ensure that the population of cells are pure.

Using this method, NIH-3T3 fibroblasts were co-transfected by calcium phosphate precipitation with the pKO neo plasmid and either pLTR CO12, encoding the full length human EGF receptor, or pLTR HC2, encoding the mutant Type III EGF receptor from a human GBM tumor. After G418 selection, clones were evaluated for expression of the human EGF receptor by Western blotting of cell lysates. Cells overexpressing the receptor to a similar level to that expressed by A431 human epidermoid carcinoma cells were identified. A cell line overexpressing the intact human EGF receptor, hereinafter referred to as CO12 20c2, was identified. Cell lines overexpressing the mutant EGF receptor were also identified. Examples of these cell lines include, but are not limited to, HC2 20d2, HC2 20d1, HC2 20d4, NM#3 HC2 20d2/c, HC2/NS1 and derivatives thereof.

Cells lines overexpressing the mutant EGF receptor grew in soft agar in the absence of EGF. The addition of EGF did not enhance the colony formation. In contrast, clones which produced much lower levels of the mutant EGF receptor such as HC2 20cl grew very little without the added EGF, and although colony formation was enhanced by EGF, this clone exhibited a much lower cloning efficiency than clones which overexpress the mutant EGF receptor.

Cell lines which overexpress the mutant EGF receptor have also been found to exhibit endogenous receptor activation. When the transfectant clones were initially analyzed by immunoblotting with an antibody specific for the human EGF receptor, the amount of receptor produced by the various clones varied considerably with some clones producing more receptor. Immunoblotting analysis of the same lysates (prepared from cells which were not treated with EGF) with a monoclonal antibody specific for the activated form of the human EGF receptor indicated that some of the lysates contained activated EGF receptors; however, activation was detectable only in those lysates which contained a substantial level of EGF receptors. The HC2 20d2 lysates showed a similar level of activated EGF receptor to A431 cells which had been treated with EGF.

Immunocytochemistry was performed on these cell lines using an antibody to the EGF receptor. The HC2 20d2 clone stains more intensely than CO12 20c2 and has the morphology of a transformed cell line. HC2 20cl, which expresses much less of the mutant protein than HC2 20d2, stains very weakly with this antibody, and has a morphology more like that of normal 3T3 cells. When stained with the antibody for the activated human EGF receptor, many HC2 20d2 cells in culture which were not treated with EGF reacted positively, whereas very few CO12 20c2 cells stained with antibody. Very few cells of the HC2 20cl clone showed any reaction to the anti-activated human EGF receptor antibody, and those that did reacted weakly. Treatment of CO12 20c2 clones expressing normal human EGF receptor with EGF (20 ng/ml) for as little as 5 minutes resulted in an increase in the intensity and number of cells staining with anti-activated EGF receptor antibody. Within an hour, nearly all cells in cultures of CO12 20c2 were positive for the activated EGF receptor and the cells underwent morphologic changes. In contrast, the cell lines of the present invention stained with anti-activated antibody without the addition of EGF.

It appears that much of the mutant EGF receptor is intracellular. Immunocytochemical staining of formalin-fixed cells without treatment with Triton X-100 resulted in relatively weak surface staining of the various transfectant clones. However, observation of preparations stained after Triton X-100 treatment revealed dark, apparently intracellular accumulation of the mutant EGF receptor, especially apparent in clone HC2 20d2. Staining with the antibody to the activated form of the EGF receptor also showed a perinuclear "cap" of activated receptor within many cells of this clone. In order to quantitatively compare the location of the EGF receptors in transfectant clones expressing the normal or mutant EGF receptor, cells were fixed, incubated with antibody to the EGF-binding domain of the EGF receptor with or without treatment with Triton X-100, and labeled with $^{125}$I-secondary antibody. Measurement of the solubilized radioactivity indicated that 52 to 60% of the EGF receptors are on the surface of the cells in the transfectant clones, compared to about 70% in A431 human epidermoid carcinoma cells. This analysis also demonstrated that the HC2 20d2 and CO12 20c2 clones have EGF receptor densities on the same order as A431 cells. A431 and CO12 20c2 clones bound similar amounts of $^{125}$I-EGF. In contrast, HC2 20d2 cells, which expressed the highest levels of EGF receptors based on Western blotting and immunocytochemistry, failed to bind $^{125}$I-EGF significantly in this assay.

Signal transduction was found to be altered in clones overexpressing the mutant EGF receptor. Analysis by Western blotting of the cellular proteins containing phosphotyrosine provided additional evidence of the endogenous activation of the mutant EGF receptor in the HC2 20d2 clones. The EGF receptor is phosphorylated in these cells even after 48 hours in serum-free medium, whereas very little phosphotyrosine is detectable under these conditions in CO12 20c2 or A431 cells. Furthermore, while incubation with EGF prior to cell lysis causes a rapid increase in the phosphorylation of the EGF receptor, as well as many other proteins, in both CO12 20c2 and A431 cells, little or no change is seen in the tyrosine phosphoproteins in HC2 20d2. Furthermore, a difference is apparent in the total set of tyrosine-phosphorylated proteins in HC2 20d2 compared with CO12 20c2. Specifically, although the proteins which are phosphorylated in the HC2 20d2 cells are also present in EGF-stimulated CO12 20c2 cells, there appear to be fewer bands present in the former than in the latter. Besides the EGF receptor itself, the major phosphoproteins present in both clones are in three main bands of apparent molecular weights of ca. 55–66 kDa, 33–37 kDa, and 22–26 kDa. These same proteins are also tyrosine-phosphorylated in EGF-stimulated A431 cells. This difference in phosphorylation patterns is not solely due to the long term stimulation by the mutant EGF receptor, inasmuch as similar stimulation by the normal EGF receptor via the addition of EGF does not result in the same pattern in either A431 or CO12 20c2 cells. Utilizing an affinity column specific for the Type III mutant EGF receptor, it has been shown that proteins in the ca. 35 and 55–66 kDa tyrosine-phosphorylated bands seen in whole HC2 20d2 lysates do associate with these receptors, even in the absence of EGF stimulation, suggesting that these proteins are involved in signal transduction from the EGF receptors and that these cell lines are an excellent source for purifying these proteins.

Cell lines expressing low levels of mutant receptor do not have high levels of EGF receptor activity, nor will they form tumors when injected into mice. Because of their unique properties, the clones and cell lines containing these clones of the present invention are useful in a number of different applications. Specifically, these cell lines or tumors formed in mice from these cell lines can be used to evaluate compounds which inhibit the EGF receptor without the addition of EGF. Other cell lines require addition of EGF to perform such studies making such experiments more costly and less convenient. Thus, the cell lines of the present invention provide a cost effective and convenient means for screening compounds that potentially act upon the EGF receptor. Cells in culture can be treated with the test compound and then assayed for either morphologic evidence of the reversion of the transformed phenotype, decreased cell growth, a decrease in the phosphotyrosine content of the treated cells, or a decrease in kinase activity of the mutant receptor. In addition, the tumors formed by these cell lines in mice provide a useful model for evaluating tumor vaccines, monoclonal antibodies or antisense compounds directed against the mutant receptor. Mice bearing tumors from injection of this cell line are useful in producing and evaluating agents involved in the immune response to this tumor. The mice may be treated with a test agent and then injected with cell lines of the present invention to see if the agents prevent tumor formation or retards tumor growth. Alternatively, mice may be injected with cell lines of the present invention first and then treated with the test agent to see if this agent causes regression in tumor size or prolongation of survival. Since the receptor is constantly active in these cell lines, they also can be used to study proteins and/or genes involved in the biochemical pathway of this receptor and the genesis of tumors. The cell lines of the present invention can also be used in the identification of and a source of proteins and corresponding cDNA clones that are involved in the signal transduction pathway of the EGF receptor and in tumorigenesis. Tyrosine phosphorylated proteins produced from these cell lines can be purified using affinity chromatography. The sequences of these proteins are then determined by protein microsequencing techniques to derive nucleic acid information. This information is used to obtain cDNA clones. cDNA clones involved in tumorigenesis are obtained by subtraction cDNA hybridization methods using cDNA from parental cells to subtract from cDNA derived from the cells of the present invention.

The cell lines of the present invention can also be used as an immunogen to raise antibodies. Injection of these cells elicited an antibody response that was specific for the mutant receptor which yielded antibodies of higher affinity than that elicited by the peptide alone. Immunization with the synthetic 14 amino acid peptide spanning the junction did not elicit anti-EGFR type III activity in mice and macaques (Wikstrand et al. *J. Neuroimmunol.* 1993, 46, 165–174). However, the production of high affinity murine anti-EGFR Type III monoclonal antibodies was achieved by immunization with the EGFR Type III molecule, either as a component of the intact cell surface or of microsomal preparations from the cell lines of the present invention. Various procedures known in the art may be used for the production of these antibodies. Such antibodies include, but are not limited to, polyclonal, monoclonal, chimeric, single chain, Fab fragments and an Fab expression library. In one embodiment, the cells may be mixed with adjuvant and injected into various host animals, including but not limited to, rabbits, mice, rats, goats and horses.

Peptides, proteins or fragments thereof produced from these cell lines which are capable of specific immunoactivity can also be used in the present invention to raise antibodies against. These peptides, proteins or fragments thereof can be conjugated to an immunogenic carrier. Adjuvants may also be administered in conjunction with the peptide or protein to increase the immunologic response of the host animal.

Adjuvants which may be used in the present invention include, but are not limited to, complete and incomplete Freund's, mineral gels such as aluminum hydroxide, surface active substances such as lysolecithin, pluronic polyols, polyanions, peptides and oil emulsions.

Monoclonal antibodies raised against the cell lines or peptides or proteins expressed by the cell lines of the present invention can be prepared using any technique which provides for the production of antibodies by continuous cell line in culture. For example, monoclonal antibodies L8A4, Y10 and H10 were prepared by immunizing Balb/c mice with a combination of either HC2 20d2 cells and the synthetic 14 amino acid peptide; HC2 20d2 cells, HC2 20d2 microsomal membranes and the synthetic 14 amino acid peptide; or HC2 20d2 microsomal membranes and the synthetic 14 amino acid peptide, respectively. Such techniques are well known to those of skill in the art and include, but are not limited to, the hybridoma technology originally described by Kohler and Milstein, *Nature* 1975, 256, 495–497, the human B-cell hybridoma technique described by Kosbor et al., *Immunology Today* 1983, 4, 72 and the EBV-hybridoma technique described by Cole et al., *Monoclonal Antibodies and Cancer Therapy*, Alan R. Liss, Inc., pp 77–96.

Antibodies raised against the cell lines or peptides or proteins expressed by these cell lines can then be used to screen for the presence and subcellular distribution of similar peptides in biological samples. Using the monoclonal antibodies L8A4 and Y10, it has been demonstrated that the incidence of EGFR type III expression in gliomas is even higher than originally projected. Further, EGFR type III was readily detectable in breast and non-small cell lung carcinoma. This mutant receptor has also been identified in ovarian tumors.

In addition, monoclonal antibodies of the present invention can be used as therapeutics. For glial tumors, there have been several clinical trials using antibodies against the EGF receptor conjugated to either radionuclides or toxins to effect tumor cell killing (Brady et al., *Intl J. Rad. Onc, Biol, Phys.* 1992, 22(1), 225–30; Masui et al., *Cancer Research* 1989, 49(13), 3482–8; Mendelsohn, J., *Sem Can Biol* 1990, (5), 339–44; Mendelsohn, J., *J. Steroid Biochem & Mol Biol* 1990, 37(6), 889–92; Sawamura, Y and DeTribolet, N., *J. Neurosurgical Sci* 1990, 34(3–4), 265–78). This approach takes advantage of the fact that glial tumors express very high levels of the protein; however, outside the brain there are several organs, notably the liver, that express comparable amounts of the proteins. Therefore, specificity with these antibodies remains a problem. In the present invention, however, antibodies are raised against the mutant epitope thereby providing specificity and decreasing systemic toxicity.

The rate and extent of internalization of monoclonal antibodies L8A4, H10 and Y10 was examined. All three monoclonal antibodies were internalized by HC2 20d2 cells. The rate and percentage of monoclonal antibody entering the cells differs slightly for L8A4 and Y10 compared to H10. Less mAb H10 is lost from the cell surface, and a smaller percentage of the cell culture supernatant-associated counts are TCA-soluble, indicating that a fraction of the intact H10 dissociates from the cells before internalization and degradation. In vivo biodistribution studies indicated that two of these mAbs, namely L8A4 and H10, specifically localize to EGFR-expressing tumor xenografts established in nude mice. Accordingly, it is believed that antibodies raised against cell lines of the present invention can serve as effective delivery agents for chemotherapeutic agents useful in the treatment of cancer. Antisense oligonucleotides targeted against the mutant Type III EGF receptor are also provided in the present invention. In a preferred embodiment, the antisense oligonucleotide contains sequences from what were formerly distant portions of the normal EGF receptor cDNA. This would include antisense nucleotide sequences that are proximal to and including nucleotide 274 as defined by Ullrich et al., *Nature* 1984, 309, 418–425, joined to antisense nucleotide sequences that are distal to and including nucleotide 1076. In a preferred embodiment, this would comprise the sequence 5'-CATAATTACCTTTCTTTT-3' (SEQ ID NO: 2). As will be recognized by those of skill in the art upon this disclosure, similar sequences containing modifications or variations in length can also be used in the present invention but an essential characteristic is that the sequence must contain 5' TACCTT 3'. These antisense oligonucleotides have been found to down regulate the mutant receptor. The use of antisense oligonucleotides to inhibit viral replications has been used by numerous researchers as tools for selectively knocking out the expression of a wide variety of both viral and endogenous transcripts. Considerable advances have been made in the understanding of how antisense works and methods of making these oligonucleotides more effective. Antisense agents made from either DNA or RNA are in wide use. Antisense DNA employs oligodeoxynucleotides where the typical oligomer is from 14 to 21 nucleotides in length. Effective inhibition has been observed from 1 to 50 $\mu$M. The use of mammalian expression vectors to express antisense RNA sequences can also be used if degradation or rapid clearance is of concern since the antisense transcript is being constantly and endogenously produced. Antisense oligodeoxynucleotides against the basic fibroblast growth factor receptor have been used by Morrison to specifically inhibit the growth of the human glioma cell line SNB-19 (Morrison, *J. Biol Chem* 1991, 266(2), 728–34). A 50 $\mu$M concentration of antisense primer resulted in 80% inhibition of growth. Antisense RNA against the EGF receptor has been used successfully by two different laboratories to inhibit the growth of the squamous cell lines NA and KB (Moroni et al., *J. Biol Chem* 1992, 267, 2714–2723; Yamada et al., *Exp Cell Res* 1989, 184, 90–98). Both groups were able to demonstrate a reduction in the amount of protein correlated with a decrease in the growth properties of these cells. It has also been shown that antisense RNA against the IGF-I gene not only reduced the amount of protein, but also enhanced immunogenicity of already existing tumor (Trojan et al., Science 1993, 259, 94–97).

In the present invention, oligonucleotides targeted to the mutant receptor were synthesized by standard B-cyanoethyl phosphoramidite chemistry and purified by ethanol precipitation. Other methods of synthesis routine to those of skill in the art can also be used. For example, an antisense oligomer having the sequence 5' -CATAATTACCTTTCTTTT-3' (SEQ ID NO: 2) was synthesized. A sense oligomer having the sequence 5' -AAAAGAAAGGTAATTATG -3' (SEQ ID NO: 3) was also synthesized. Cells of the present invention which overexpress the mutant EGF receptor were treated with either 2.5, 10, or 40 $\mu$M sense or antisense oligonucleotide. Fresh oligomer was added every day for a total of four days. The cells were then lysed, run on SDS-PAGE and transferred to nitrocellulose. The blot was incubated with an antibody against the mutant receptor. It was found that there is preferential down regulation of the mutant receptor in cells treated with antisense, which is very apparent at the 40 $\mu$M dose. Accordingly, these antisense agents can be used to decrease the expression of this mutant receptor.

The following nonlimiting examples are provided to further illustrate the invention.

EXAMPLES

Example 1

Construction of Expression Vectors

A full length EGF receptor cDNA that has been completely sequenced was used as the basis for the generation of mutant receptors. The plasmid construct pCO12 which contains the normal human EGF receptor cDNA was obtained from NCI, and corresponds to the sequence of the cDNA determined by Ullrich et al., Nature 1984, 309, 418–425. The EGF receptor cDNA was cloned into the mammalian expression vector pLTR-2 which drives transcription using the Moloney murine leukemia virus long terminal repeat (LTR) promoter. This construct was called pLTR2-CO12. To derive a construct expressing the Type III EGF receptor mutant, a portion of the Type III EGF receptor cDNA was cloned from a cDNA library made from a human glioblastoma tumor, D270, that overexpresses this particular mutant. A 251 bp Sst I-Dra I fragment that encompasses the abnormal fusion junction was ligated to a 2.9 kb DraI-XhoI fragment from pCO12. This construct, called pLTR2-HC2, would express the mutant EGF receptor but was otherwise identical to the construct expressing normal EGF receptor.

Example 2

Transfection and Derivation of Cell Lines

Expressing High Levels of the Mutant EGF Receptor

NIH-3T3 cells were obtained from the ATCC. The NIH-3T3 cell line was maintained in DMEM with 10% calf serum. NIH-3T3 cells were plated at 1×10$^6$ cell/100 mm dish. The medium was changed the next day and the cells were transfected 3 hours later using a modified version of the standard calcium phosphate transfection method. Cells were co-transfected with either pLTR CO12, pLTR-HC2 or pLTR2 vector only, plus the pKOneo (2 $\mu$g) at 10:1 and 20:1 (w/w) ratios. The medium was replaced the next day and 2 days later the cells in each plate were trypsinized and split 1:5 in 10% calf serum medium containing 350 $\mu$g/ml G418 sulfate (complete medium) (Gibco/BRL, Gaithersburg, Md.). Within 2 weeks, individual G418-resistant colonies were present. These were picked and expanded first into 25 cm$^2$ flasks and then into 75 cm$^2$ flasks. When enough cells were present, the subclones were first analyzed by Western blot for the levels of protein as described below. Screening for protein amounts first was the most efficient method for obtaining subclones with the desired level of protein expression and was crucial to deriving clones with high levels of expression. A total of 32 CO12 and 34 HC2 clones were evaluated by Western blotting. When suitable clones were found, they were expanded and then analyzed by Southern blot to verify genomic integration. Four HC2 clones produced detectable levels of the mutant EGF receptor. To ensure that the cell lines had high, uniform levels of expression, each cell line was seeded into soft agar as described in Example 4.

Example 3

Western Blotting and Immunodetection of Human EGF Receptors and Tyrosine-Phosphorylated Proteins Cells were lysed in PBS/TDS buffer (10 mM dibasic sodium phosphate, 150 mM sodium chloride, 1% Triton X-100, 0.5% sodium deoxycholate, 0.1% sodium dodecyl sulfate, 0.2% sodium azide, and 0.004% sodium fluoride) containing 1 mM sodium orthovanadate, pH 7.25. Protein concentrations were determined by the Bradford Dye binding method (BioRad, Hercules, Calif.). Lysates were mixed with equal volumes of 2×sample buffer containing 6% SDS and 10% β-mercaptoethanol, boiled for 3 minutes and electrophoresed on 7.5% SDS-PAGE gels with 3.5% polyacrylamide stackers in a discontinuous buffer system. Proteins were transferred to nitrocellulose membranes with a semi-dry transfer apparatus and the membranes were blocked in blotto/TTBS. Membranes were incubated with primary antibody in blotto/TTBS for two hours. Antibodies against intracellular epitopes of the human EGF receptor (Clone Z025) or the activated form of the human EGF receptor (Clone Z026) were from Zymed Immunochemicals (San Francisco, Calif.) and were used at concentrations of 0.5 $\mu$g/ml; antibodies against phosphotyrosine (Clone 4G10) were from Upstate Biotechnology Inc. (Lake Placid, N.Y.), and used at a concentration of 1 $\mu$g/ml. After washing with TTBS, blots were incubated for 1 hour with $^{125}$I-Sheep Anti-mouse Ig F(ab')$_2$ (Amersham, Arlington Heights, Ill.) at 0.3 $\mu$Ci/ml and exposed at −80° C. for 1 to 3 days.

Example 4

Soft Agar Cloning of Cell Lines to Derive the HC2 20d2 Series of Cell Lines That Express High Levels of the Mutant EGF Receptor Soft-agar cultures were prepared using low-gelling temperature agarose (Type VII, Sigma Chemical Co., St. Louis, Mo.). Underlays containing 10% calf serum complete medium plus 0.6% agarose were dispensed (2 ml/35 mm dish) and allowed to gel at room temperature. Cells were trypsinized from subconfluent cultures and plated at 5,000 cells/dish in 1 ml of complete medium with 0.3% agarose, with or without 20 ng/ml EGF. Cultures were re-fed on days 7 and 14 and were counted on day 21. Colonies larger than 60 $\mu$m diameter were counted.

Following the selection of cell lines, immunocytochemical analysis revealed that the level of expression could vary considerably from cell to cell in a given cell line. Thus, several cell lines were further subcloned in an effort to obtain a series that expressed uniformly high levels of mutant receptor. Cells were plated in soft agar as described, and large colonies which formed in the absence of EGF were picked and expanded in monolayer culture. The cells were then analyzed for expression of the mutant receptor by both Western Blotting and immunochemistry. This resulted in the selection of several subclones by this method that expressed various levels of the mutant EGF receptor. The subclones designated HC2 20d2/b and HC2 20d2/c expressed similar, very high levels of the mutant EGF receptor, which were equivalent to that observed in some human glioblastoma tumors. These new cell lines were expanded and frozen stocks prepared at low passage; this was essential inasmuch as the level of expression of the mutant receptor gradually declined in vitro although substantial expression is maintained through ten 1:100 passages.

Example 5

Tumorigenicity in athymic mice

HC2 20d2/c cells were tested for tumorigenicity in six week old nude (BALB/c nu/nu female) mice. $1 \times 10^6$ cells in 0.25 ml of PBS were injected s.c. in the hind flank of six mice. Mice were palpated biweekly and observed for 2 months. Tumors were detectable within one week in most animals and all animals had to be sacrificed by 2 months as a result of the rapidly growing tumors. All tumors continued to express high levels of mutant EGF receptor, and G418-resistant cell lines were readily established from the excised tumors. One such cell line, designated NM#3 HC2 20d2/c, was used for all subsequent tumorigenicity studies.

Example 6

Tumorigenicity in NIH-Swiss mice

After determining that HC2 20d2/c were tumorigenic in athymic mice, their tumorigenicity in syngeneic mice with normal immune function was investigated. NIH-Swiss mice were injected as above with $10^4$, $10^5$, $10^5$ or $10^7$ cells; 2 animals per dose. Animals given either $10^6$ or $10^7$ cells developed tumors within one week and these continued to grow for several weeks before regressing in 3 of the 4 animals in this experiment. The tumor in one of the $10^7$ dose animals continued to grow until it was necessary to sacrifice the animal. A G418-resistant cell line was established from this tumor and these cells, designated HC2/NS1, continued to express a high level of the mutant human EGF receptor.

Example 7

Peptide Vaccine

The peptide encompassing the novel sequence at the fusion junction present in the mutant human EGF receptor (LEEKKGNYVVTDHC (SEQ ID NO: 1) was synthesized by standard methods; the carboxy-terminal cysteine residue was included to facilitate the conjugation of the peptide to the carriers keyhole limpet hemocyanin (KLH) and bovine serum albumin (BSA) using the heterobifunctional reagent maleimidobenzoyl- N-hydroxy-succinimide ester (MBS). These conjugates are designated "KLH-LEEK" and "BSA-LEEK"; the former was used for all vaccinations and the latter for the titering of serum antibodies. For initial vaccinations, mice (female NIH-Swiss) were injected with 0.1 ml s.c. with an emulsion of equal parts Freund's complete adjuvant and KLH-LEEK at 100 µg/ml in PBS. Subsequent injections used Freund's incomplete adjuvant.

Example 8

Cytotoxic T Lymphocyte Assay

The spleens of sacrificed animals were removed, rinsed with PBS and disrupted by standard methods. After washing, the cells were plated in RPMI 1640 containing 10% FBS, $5.5 \times 10^{-5}$ M β-mercaptoethanol, 0.1 mM Eagle's MEM nonessential amino acids (NEAA), 100 units/ml penicillin, 100 µg/ml streptomycin, and 100 µg/ml kanamycin, plus 2 µg/ml of either concanavalin A or LEEK-peptide. Spleen cells were incubated at 37° C. in a humidified incubator with 5% $CO_2$ for 3 to 4 days prior to use in cytotoxic T lymphocyte (CTL) assays. Assays were carried out by standard methods well known in the art, or by the following modification: target cells (NM#3 HC2 20d2/c as specific targets; CO12 20c2/b, an NIH-3T3 transfectant clone over-expressing the normal human EGF receptor were used as non-specific control targets) were plated at 200,000 cells/16 mm well in 24 well Falcon tissue culture plates and incubated for 3 days before use. Target cells were labelled in situ for 1 hour with 100 µCi/$1 \times 10^7$ cells of $^{51}$Cr, washed 3× and the effector cells were added at various ratios to triplicate wells. Plates were incubated for 4 to 5 hours and aliquots were quantitated in a gamma counter to determine the degree of specific lysis.

Example 9

Antisense Oligonucleotides Against the Mutant Receptor

The sequence of the antisense oligomer used was 5'-CATAATTACCTTTCTTTT -3' (SEQ ID NO: 2). The sequence of the sense oligomer used was 5' -AAAAGAAAGGTAATTATG -3' (SEQ ID NO: 3). The oligonucleotides were synthesized by standard B-cyanoethyl phosphoramidite chemistry and purified by ethanol precipitation.

$1 \times 10^5$ HC2 20d2/c cells were seeded into 35 mm$^2$ wells and 24 hours later the cells were treated with either 2.5, 10, or 40 µM sense or antisense oligonucleotide. Fresh oligomer was added every day for a total of four days. The cells were then lysed, run on SDS-PAGE and transferred to nitrocellulose. The blot was then incubated with an antibody against the mutant receptor. This shows that there is preferential down regulation of the mutant receptor in cells treated with antisense, which is very apparent at the 40 µM dose.

Example 10

Preparation and Characterization of Monoclonal Antibodies Against the Mutant Receptor Pep 3, a 14 amino acid peptide corresponding to the predicted amino acid sequence at the fusion junction was synthesized, purified and coupled to keyhole limpet hemocyanin by Anaspec Inc. (San Jose, Cailf.). A 10 amino acid peptide of unrelated structure, Pep 1, served as a negative control.

The cell line HC2 20d2 was obtained by transfection of NIH 3T3 cells as described in Example 2.

To prepare microsomal membrane fractions, 10 grams of HC2 20d2 cells or A431 athymic mouse xenografts were homogenized in 20 mM Tris Buffer, pH 7.4, containing 0.3 M sucrose and 1 mM phenylmethylsulfonyl fluoride, at 4° C. The homogenates were spun at 15,000×g for 20 minutes. The supernatants were then spun at 150,000 ×g for 30 minutes. The resulting pellet was washed by ultracentrifugation until the supernatant was free of protein. The final pellet was resuspended in 1 ml of 115 mM phosphate buffer per gram of tissue homogenized and stored at –135° C.

Four combination immunization protocols, as detailed in the following Table, used the following immunogens: Pep 3 conjugated to keyhole limpet hemocyanin in a 1:1 emulsion in Dulbecco's phosphate buffered saline (DPBS) with complete Freund's adjuvant (Difco, Detroit, Mich.), incomplete Freund's adjuvant, or in DPBS alone; collagenase-disaggregated D-270MG xenograft cells (D-270 MG-X); cultured HC2 20d2 cells harvested with 0.02% EDTA-DPBS; and microsomal membrane preparations of HC2 20d2 xenograft cells. BALB/c female mice, 8 to 15 weeks of age at the initiation of immunization, were used. In general, reciprocal 50% end point titers in excess of 5000 versus Pep 3 and the receptor target was required before fusion.

TABLE

Anti-EGFR type III mAbs

| Protocol | Immunization Regimen | mAB obtained | IgG class |
|---|---|---|---|
| 1 | Days 1, 157; Pep 3-KLH | J2B9 | IgG1 |
|   | Days 56, 132; D270 MG-X cells | J3F6 | IgG1 |
|   | Day 161; fusion | | |
| 2 | Days 40, 103; Pep 3-KLH | L8A4 | IgG1 |
|   | Days 1, 25, 74, 87; HC2 20d2 cells | | |
|   | Day 107; fusion | | |
| 3 | Day 199; Pep 3-KLH | Y10 | IgG2a |
|   | Days 1, 213; HC2 20d2 cells | | |
|   | Days 161, 175; HC2 20d2 microsomal membranes | | |
|   | Day 216; fusion | | |
| 4 | Day 68; Pep 3-KLH | H10 | IgG1 |
|   | Day 1; HC2 20d2 microsomal membranes | H11 | IgG1 |
|   | Days 83, 177, 194; Pep 3-KLH + HC2 20d2 microsomal membranes | | |
|   | Day 197; fusion | | |

Fusions were performed with the nonimmunoglobulin-secreting Kearney variant of P3X63/Ag8,653 in accordance with standard procedures as described by Wikstrand et al. *J. Neuroimmunol.* 1982, 3, 4362. Supernatants were screened for positivity on Pep 3 and D-270 MG-X or HC2 20d2 and for lack of reactivity for non-transfected NIH 3T3 cells and A431 (normal EGFR. Hybrids derived in Protocol 4 were initially screened on HC2 20d2 extract preparation for positivity and A431 extract preparation to determine specificity.

Antibody titers against plated peptides were determined by ELISA and RIA. A capture ELISA assay using, sequentially, sheep anti-EGFR intracellular domain antiserum (Life Technologies, Grand Island, N.Y.) as capture reagent, antigen extract, prospective anti-EGFR type III supernatants, and sheep antimouse IgG Fc was used to screen Protocol 4 hybridomas. RIA was used to determine reactivity against cell lines expressing EGFR type III. A modified Scatchard analysis was used to measure the binding affinity of Iodogen-catalyzed iodinated mAbs, beginning with serially diluted radiolabeled antibody at 10 µg/ml versus HC2 20d2 and NIH 3T3 cells. Data were analyzed using the Equilibrium Binding Data Analysis Program (Biomedical Computing Technology Information Center, Nashville, Tenn.). Ascertainment of recovered cells at the end of the procedure allowed calculation of the number of EGFR type III sites per cell. Iodinated anti-EGFR type III mAbs were also analyzed by competitive binding assay: 50 ng of each iodinated mAb was reacted with acetone-fixed HC2 20d2 cells in the isotype controls to 1000-fold excess (50 µg/ml). After being incubated at 37° C. for 2 hours, plates were washed, and $^{125}$I counts bound per well were determined.

Example 11

Immunohistochemical and RT-PCR Analysis of Normal and Neoplastic Human Tissues

Purified mAbs were screened against acetone-fixed HC2 20d2, NIH 3T3 and A431 monolayers or acetone-fixed frozen sections of D-256 MG and D-245 MG glioma xenografts passaged in athymic rats. It was determined the mAbs L8A4 and Y10 were the most optimal reagents for immunohistochemistry. They were incorporated into an antibody panel consisting of Pep 3 affinity-purified rabbit antiserum, mAb 528 and mAb 3B4 (pan human tissue positive control). Mab 528 was included for immunohistochemical analysis because it reacts with an epitope common to the extracellular domain of both wild-type EGFR and EGFR type III. Immunohistochemical analysis was performed on acetone-fixed (−70° C., 30 seconds), 5 to 8 µm tissues sections of normal or tumor tissue plated on Labtek slides in accordance with procedures described by Humphrey et al. *Cancer Res.* 1988, 48, 2231–2238. Tissues examined include 11 cases of breast carcinoma, 31 cases of glioma and a panel of 35 samples of normal tissues.

RNA was isolated from sections of 10 of the 11 breast carcinoma samples and analyzed for EGFR type III expression using RT-PCR. RNA was purified from 2×20 µm sections of each sample using the guanidium isothiocyanate-acid phenol method as described by Chomczynski, P. and Sacchi, N. *Anal Biochem.* 1987, 162,156–159. Three micrograms of total RNA was combined with 100 ng random hexamer primer (GIBCO-BRL, Gaithersburg, Md.) and RNasin (Promega, Madison, Wis.); the solution was heated at 68° C. for 10 minutes, then placed on ice. Dithiothreitol (0.1 M), dNTPs (10 mM each), Superscript reverse transcriptase (GIBCO-BRL), 5×Superscript buffer and water were added and the mixture was heated at 37° C. for 15 minutes, then 43° C. for 60 minutes. The cDNA synthesis reaction was terminated by heating at 98° C., and the mixture was stored at −80° C. PCR was performed using 2 µl cDNA in a total reaction mixture volume of 75 µl containing 2.5 units Taq DNA polymerase (Promega); Taq buffer containing 1.5 mM Mg+2, 0.6 µM EGFR forward primer and 0.6 µM EGFR reverse primer; and 200 µM deoxynucleotide triphosphates. A hot start technique was used. Forty cycles of amplification were performed [95° C. for 80 seconds, 54° C. for 1 minute, and 72° C. for 2 minutes], and final elongation was performed for 10 minutes. A negative control lacking template was run with the reaction. Products were analyzed by electrophoresis on 2.0 agarose gels in triacetate-EDTA buffer (0.02 M Tris- acetate- 0.001 M EDTA) using 100 bp markers (GIBCO-BRL) as size standards, followed by ethidium bromide staining. Primers for PCR of wild-type EGFR and or variants were forward 5'-GGGGAATTCGCGATGCGACCCTCCGGG-3' (SEQ ID NO: 7) and reverse 5'-GGGAAGC-TTTCCGTTACACACTTTGCG-3' (SEQ ID NO: 8). Eighteen bases in each primer were complementary to the nucleotide sequences for human EGFR. Each primer also included an artificially introduced restriction site at its 5' end to facilitate the cloning of the resultant PCR products into pBluescript vector (Stratagene, La Jolla, Calif.) for sequence analysis. When these primers are used, the sizes of the expected normal and EGFR type III products are 1037 and 236 bp, respectively. Products corresponding to PCR amplification of EGFR type III mRNA were present in 3 out of 3 breast carcinoma tissues that were reactive with L8A4 mAb immunohistochemically. In addition, bands corresponding to EGFR type III were detected in five additional breast carcinomas that had demonstrated no immunohistochemical reactivity with mAb L8A4.

Example 12

Western Blot Analysis of Tumor Lysates

Tumors were homogenized in PBS/TDS buffer (10 mM Na2HPO4, 150 mM NaCl, 1% Triton X-100, 0.5 % sodium deoxycholate, 0.1% SDS, 0.2% sodium azide, and 0.004% sodium fluoride (pH 7.25) containing 1 mM sodium orthovanadate. Protein concentrations were determined by the BioRad DC assay (BioRad, Richmond, Calif.). Lysates (50 to 150 μg) were electrophoresed on 6% (0.75 mM) or 4–20% (1.0 mm) SDSD-PAGE gels. Gels were transferred to nitrocellulase membranes (Schleicher and Schuell, Keene, NH) by using a standard protocol. Membranes were blocked in Blotto/TTBS [100 mM Tris (pH 7.5) 150 mM NaCl and 0.1% Tween 20 containing 5% nonfat milk]. The blots were then incubated with 1 μg/ml of anti-EGFRvIII or monoclonal antibody against an intracellular epitope of the human EGF receptor (Zymed, San Francisco, Calif.) in Blotto/TTBS for 2 hours at room temperature, washed four times in TTBS, and then incubated with 0.23 μCi.ml of 125I antirabbit IgG or antimouse IgG antibody (Amersham, Arlington Heights, Ill.) for 1 hour, washed four times, dired and exposed to film.

Example 13

Radioassay for mAb Internalization

Radiolabeled antiEGFR type III mAbs were incubated with HC2 20d2 cells in antibody excess (2.5 μg/$10^6$ cells, determined by analytical flow cytometry) for 1 hour at 4° C. Unbound mAb was removed by washing with cold 1% BSA/PBS, and cell density was readjusted to 2×$10^6$ cells/ml in Zinc Option culture medium containing 10% FCS. The cells were aliquoted into 500 μl samples, and the culture temperature was adjusted to 37° C. Samples were processed by the following procedure at 0, 1, 2, 4, 8 and 20 hours: cells were pelleted, and the culture supernatants were removed and saved for counting. Two 600 μl acid washes with Zinc Option (pH 2.0) were performed with intervening incubations at 4° C. for 15 minutes. The cells were pelleted, and the acid washes were combined and counted with cell pellets and cell culture supernatants in a γ counter. The counts in the initial cell culture supernatant were also assayed for solubility in 12.5% trichloroacetic acid.

Example 14

Biodistribution Studies

Paired-label immunolocalization studies were performed in mice bearing subcutaneous HC2 20d2 xenografts. Athymic mice bearing 7-day-old xenografts (approximately 150–250 mm$^3$ in size) were randomized by tumor volume (calculated using the formula L×W$^2$×½, with L and W representing the longest longitudinal and transverse diameters of the tumor as measured with vernier calipers). Mice were injected via tail vein injection with 2.5 μg of L8A4 or H10 labeled with $^{125}$I using tyramine cellobiose (TCB), each paired with an equal amount of $^{131}$I-labeled isotype-matched control mAb of irrelevant specificity, P3X63Ag8. Groups of 5 mice were killed at 4, 12, 24, 48, 72, 120 and 168 hours after mAb injection. Blood samples were obtained by transection of the inferior vena cava. A complete dissection was then performed and tissues including the spleen, liver, lungs, heart, thyroid, stomach, small and large intestines, bladder, bone, skin, muscle and brain were isolated in addition to tumor. All tissues, including blood, were weighed in tared vials and assayed for $^{125}$I and $^{131}$I activity using a dual channel γcounter. Data were corrected for overlap of $^{131}$I and $^{125}$I signals and for the decay of the radioisotopes. Values for the % of injected dose/gram of tissue were derived using injection dose standards. The specificity of mAb tissue uptake was determined by calculating the localization index, expressed as cpm L8A4 or H10 per gram divided by cpm P3X63Ag8 per gram in tissue, normalized to the same cpm ratio in blood. The maximal tumor localization index (L8A4, 3.1±0.5; H10, 3.0+0.9) occurs between days 2 and 7 for both monoclonal antibodies and is relatively constant throughout that time period. Localization indices for normal tissue were between 1.0 and 1.5 for both mAbs throughout the experiment. Spleen and liver values were slightly higher but less that 2.0 on day 7 for mAb L8A4.

Estimated radiation doses to tumor xenografts and normal tissues after a hypothetical 500 μCi injection of $^{125}$I labeled mAb were determined. The % injected dose/gram of tissue for each tissue was converted to μCi/gram, and the total activity accumulated in tissues over the 7 day experiment was determined by calculating the area under the μCi/gram curves using trapezoidal integration. The μCi-hour/gram values were then multiplied by the equilibrium- absorbed dose constant for the particulate radiation of 131I.

```
                        SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
          (A) LENGTH:  14
          (B) TYPE:    Amino Acid
          (D) TOPOLOGY:  Linear (xi) SEQUENCE DESCRIPTION:   SEQ ID NO: 1:

Leu Glu Glu Lys Lys Gly Asn Tyr Val Val Thr Asp His Cys
1               5                   10

(2) INFORMATION FOR SEQ ID NO: 2:
```

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 2:

CATAATTACC TTTCTTTT                                                          18

(2) INFORMATION FOR SEQ ID NO: 3:

(i) SEQUENCE CHARACTERISTICS:
            (A) LENGTH: 18
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 3:

AAAAGAAAGG TAATTATG                                                          18

(2) INFORMATION FOR SEQ ID NO: 4:

(i) SEQUENCE CHARACTERISTICS:
            (A) LENGTH: 24
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 4:

CTG GAG GAA AAG AAA GTT TGC AAA                                              24
LEU GLU GLU LYS LYS VAL CYS GLN
1               5

(2) INFORMATION FOR SEQ ID NO: 5:

(i) SEQUENCE CHARACTERISTICS:
            (A) LENGTH: 27
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 5:

AAG TGT CCC CGT AAT TAT GTG GTG ACA                                          27
LYS CYS PRO ARG ASN TYR VAL VAL THR
1               5

(2) INFORMATION FOR SEQ ID NO: 6:

(i) SEQUENCE CHARACTERISTICS:
            (A) LENGTH: 33
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 6:

CTG GAG GAA AAG AAA GGT AAT TAT GTG GTG ACA                                  33
LEU GLU GLU LYS LYS GLY ASN TYR VAL VAL THR
1               5                   10

```
(2) INFORMATION FOR SEQ ID NO: 7:

(i) SEQUENCE CHARACTERISTICS:
        (A) LENGTH: 27
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 7:

GGGGAATTCG CGATGCGACC CTCCGGG                                              27

(2) INFORMATION FOR SEQ ID NO: 8:

(i) SEQUENCE CHARACTERISTICS:
        (A) LENGTH: 27
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 8:

GGGAAGCTTT CCGTTACACA CTTTGCG                                              27

(2) INFORMATION FOR SEQ ID NO: 9:

(i) SEQUENCE CHARACTERISTICS:
        (A) LENGTH: 8
        (B) TYPE: Amino Acid
        (C) STRANDEDNESS: Single
        (D) TOPOLOGY: Linear (iv) ANTI-SENSE: No (xi) SEQUENCE DESCRIPTION: SEQ ID NO: 9:

LEU GLU GLU LYS LYS VAL CYS GLN
1               5

(2) INFORMATION FOR SEQ ID NO: 10:

(i) SEQUENCE CHARACTERISTICS:
        (A) LENGTH: 9
        (B) TYPE: Amino Acid
        (C) STRANDEDNESS: Single
        (D) TOPOLOGY: Linear (iv) ANTI-SENSE: No (xi) SEQUENCE DESCRIPTION: SEQ ID NO: 10:

LYS CYS PRO ARG ASN TYR VAL VAL THR
1               5

(2) INFORMATION FOR SEQ ID NO: 11:

(i) SEQUENCE CHARACTERISTICS:
        (A) LENGTH: 11
        (B) TYPE: Amino Acid
        (C) STRANDEDNESS: Single
        (D) TOPOLOGY: Linear (iv) ANTI-SENSE: No (xi) SEQUENCE DESCRIPTION: SEQ ID NO: 11:

LEU GLU GLU LYS LYS GLY ASN TYR VAL VAL THR
1               5                   10
```

What is claimed is:

1. A method of inhibiting formation or growth of tumors bearing a naturally occurring Type III mutant EGF receptor in a human subject comprising inducing a cytotoxic T-cell response against the tumor by administering to said subject a vaccine comprising a peptide having at least an amino acid sequence proximal to and including the amino acid at position 5 of the corresponding normal mature EGF receptor amino acid sequence for said subject followed by a glycine and an amino acid sequence distal to and including the amino acid at position 274 of the mature normal EGF receptor.

2. A method according to claim 1 wherein the vaccine comprises a peptide having the amino acid sequence SEQ ID NO: 1.

3. A method of inducing regression of an existing tumor bearing a naturally occurring Type III mutant EGF receptor in a human subject comprising inducing a cytotoxic T-cell response against the tumor by administering to said subject a vaccine comprising a peptide having at least an amino acid sequence proximal to and including the amino acid at position 5 of the corresponding normal mature EGF receptor sequence amino acid sequence for said subject followed by a glycine and an amino acid sequence distal to and including the amino acid at position 274 of the normal mature EGF receptor.

4. A method according to claim 3 wherein the vaccine comprises a peptide having the amino acid sequence SEQ ID NO: 1.

5. A method of inducing cytotoxic T-lymphocyte activity specifically directed against tumor cells expressing naturally occurring Type III mutant EGF receptor in a human subject comprising administering to said subject a vaccine comprising a peptide having at least an amino acid sequence proximal to and including the amino acid at position 5 of the corresponding normal mature EGF receptor amino acid sequence for said subject followed by a glycine and an amino acid sequence distal to and including the amino acid at position 274 of the mature normal EGF receptor.

6. A method according to claim 5 wherein the vaccine comprises a peptide having the amino acid sequence SEQ ID NO: 1.

7. A method of immunizing a human subject against tumors bearing type III mutant EGF receptors, comprising:
(a) providing a human subject at risk for developing a tumor comprising tumor cells expressing type III mutant EGF receptors;
(b) administering a vaccine to said subject comprising a peptide having at least an amino acid sequence proximal to and including the amino acid at position 5 of the corresponding normal mature human EGF receptor amino acid sequence followed by a glycine and an amino acid sequence distal to and including the amino acid at position 274 of the normal mature human EGF receptor such that a cytotoxic T-lymphocyte activity specifically directed against said tumor cells is generated; and
(c) determining that formation of said tumor is inhibited.

8. A method according to claim 7 wherein the vaccine comprises a peptide having the amino acid sequence SEQ ID NO:1.

9. A method of immunizing a human subject against tumors bearing type III mutant EGF receptors, comprising:
(a) providing a human subject having at least one said tumor comprising tumor cells expressing type III mutant EGF receptors;
(b) administering a vaccine to said subject comprising a peptide having at least an amino acid sequence proximal to and including the amino acid at position 5 of the corresponding normal mature human EGF receptor sequence amino acid sequence followed by a glycine and an amino acid sequence distal to and including the amino acid at position 274 of the normal mature human EGF receptor such that a cytotoxic T-lymphocyte activity specifically directed against said tumor cells is generated; and
(c) determining that growth of said tumor is inhibited.

10. A method according to claim 9 wherein the vaccine comprises a peptide having the amino acid sequence SEQ ID NO: 1.

11. A method of immunizing a human subject against tumors bearing type III mutant EGF receptors, comprising:
(a) providing a human subject having at least one said tumor comprising tumor cells expressing type III mutant EGF receptors;
(b) administering a vaccine to said subject comprising a peptide having at least an amino acid sequence proximal to and including the amino acid at position 5 of the corresponding normal mature human EGF receptor sequence amino acid sequence followed by a glycine and an amino acid sequence distal to and including the amino acid at position 274 of the normal mature human EGF receptor such that a cytotoxic T-lymphocyte activity specifically directed against said tumor cells is generated; and
(c) determining that said tumor has regressed.

12. A method according to claim 11 wherein the vaccine comprises a peptide having the amino acid sequence SEQ ID NO: 1.

* * * * *